(12) United States Patent
Hall, IV et al.

(10) Patent No.: US 6,533,789 B1
(45) Date of Patent: Mar. 18, 2003

(54) DEVICE FOR ROTATIONAL STABILIZATION OF BONE SEGMENTS

(75) Inventors: Harry Thomas Hall, IV, Downingtown, PA (US); David John Little, II, Malvern, PA (US); Stephen J. Bresina, Davos Platz (CH)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/542,821

(22) Filed: Apr. 4, 2000

(51) Int. Cl.[7] ............................................... A61B 17/56
(52) U.S. Cl. ........................................................ 606/69
(58) Field of Search ............................. 606/65, 66, 69, 606/70, 71, 72, 73

(56) References Cited

U.S. PATENT DOCUMENTS

| | | | |
|---|---|---|---|
| 2,612,159 A | | 9/1952 | Collison |
| 4,095,591 A | | 6/1978 | Graham, Jr. et al. |
| 4,432,358 A | | 2/1984 | Fixel |
| 4,530,355 A | | 7/1985 | Griggs |
| 4,612,920 A | * | 9/1986 | Lower ........................ 606/66 |
| 4,657,001 A | | 4/1987 | Fixel |
| 5,007,910 A | | 4/1991 | Anapliotis et al. |
| 5,032,125 A | | 7/1991 | Durham et al. |
| 5,127,914 A | * | 7/1992 | Calderale et al. ............. 606/65 |
| 5,454,813 A | | 10/1995 | Lawes |
| 5,501,684 A | | 3/1996 | Schlapfer et al. |
| 5,514,138 A | | 5/1996 | McCarthy |
| 5,735,853 A | | 4/1998 | Olerud |
| 5,749,872 A | | 5/1998 | Kyle et al. |
| 5,843,082 A | | 12/1998 | Yuan et al. |
| 5,908,422 A | * | 6/1999 | Bresina ........................ 606/72 |
| 6,139,552 A | * | 10/2000 | Horiuchi ....................... 606/65 |

* cited by examiner

Primary Examiner—John J. Wilson
Assistant Examiner—Eduardo C. Robert
(74) Attorney, Agent, or Firm—Pennie & Edmonds LLP

(57) ABSTRACT

A device for rotational stabilization of bone segments comprising a bone plate, a bone lag screw, and a locking collar. The bone lag screw has a bone-engagement end, a distal end, and a keyed cross-sectional profile, the bone-engagement end configured for engaging a first bone segment. The bone plate has a flat portion for engaging a second bone segment and a barrel portion having an internal bore for slidably receiving the lag screw. The locking collar has a keyed internal profile that mates with the keyed cross-sectional profile of the lag screw to rotationally couple the locking collar and the lag screw when the lag screw is inserted through the locking collar, and an outer surface configured and dimensioned for (1) free rotation, in a first position, within the internal bore of the bone plate barrel portion and (2) frictionally engaging, in a second position, the internal bore of the bone plate barrel portion to resist or prevent rotation of the collar relative to the bone plate, and thereby resist or prevent rotation of the lag screw relative to the bone plate.

31 Claims, 4 Drawing Sheets

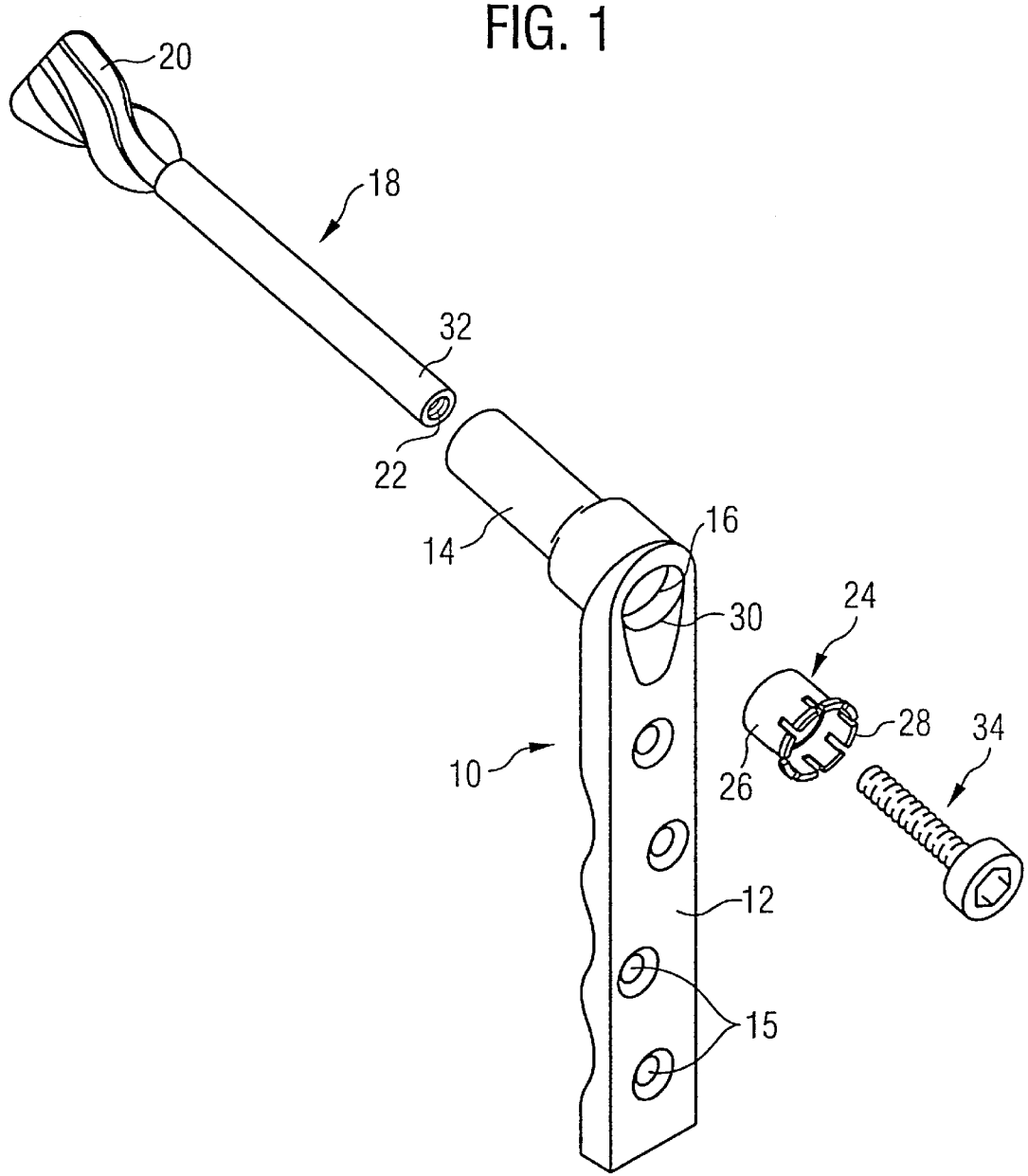

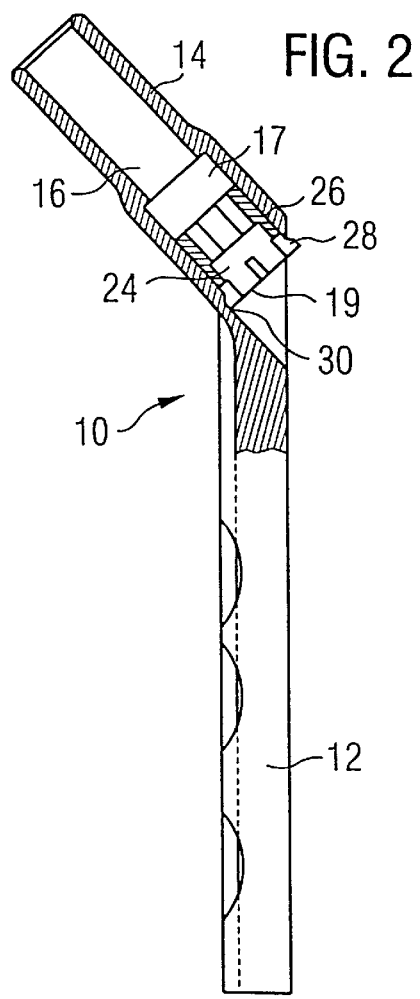
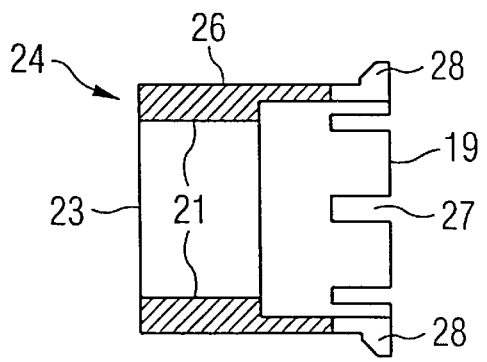
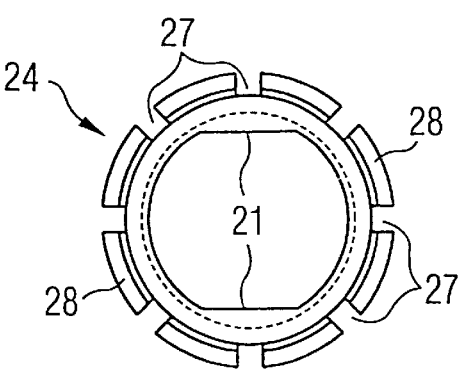

DEVICE FOR ROTATIONAL STABILIZATION OF BONE SEGMENTS

FIELD OF THE INVENTION

The present invention relates generally to connection devices, and, more particularly, to a bone connection device for rotational stabilization of bone segments.

BACKGROUND OF THE INVENTION

Devices for the repair of large bone fractures (e.g., fractures of the femoral neck) have generally consisted of some combination of a lag screw with a side plate and some means for attaching these two components to one another and to the fractured bone segments. The ability to rotationally lock a lag screw (also known as a "hip screw") relative to its side plate is very important in such devices because rotational movement of the lag screw relative to the side plate following implantation can cause premature wear of the bone fragment and result in loosening of the system prior to complete healing.

Prior art devices have attempted to rotationally lock installed lag screws using keys, pins, rings, splines, etc. See e.g., U.S. Pat. Nos. 5,007,910 and 5,514,138 to Anapliotis, et al. and McCarthy, respectively. The additional operation time and tools required to align and properly install such equipment has fueled a desire for a simpler and more effective device for aligning and rotationally locking the lag screw relative to the side plate. Such a device would reduce surgical operation time and complexity and provide a more effective and efficient mechanism for rotationally locking a lag screw to its corresponding side plate—an obvious benefit to both orthopaedic physicians and patients.

SUMMARY OF THE INVENTION

In a preferred embodiment, the present invention is a device for rotational stabilization of bone segments comprising: a bone lag screw having a bone-engagement end, a distal end, and a keyed cross-sectional profile, the bone-engagement end configured for engaging a first bone segment; a bone plate having a flat portion for engaging a second bone segment and a barrel portion having an internal bore for slidably receiving the lag screw; and a locking collar having a keyed internal profile that mates with the keyed cross-sectional profile of the lag screw to rotationally couple the locking collar and the lag screw when the lag screw is inserted through the locking collar, and an outer surface configured and dimensioned for (1) free rotation, in a first position, within the internal bore of the bone plate barrel portion and (2) frictionally engaging, in a second position, the internal bore of the bone plate barrel portion to resist or prevent rotation of the collar relative to the bone plate, and thereby resist or prevent rotation of the lag screw relative to the bone plate. The locking collar may be cylindrical, and the outer surface of the locking collar may be formed with a taper. The taper of the outer surface of the locking collar may range from about 0 degrees to about 10 degrees. The taper of the outer surface of the locking collar may be defined by a major diameter and a minor diameter, a distal end of the collar having the major diameter, and a proximal end of the collar having the minor diameter.

The internal bore of the bone plate barrel portion may also be formed with a taper and the taper of the outer surface of the locking collar may be of the same degree and profile as the taper of the internal bore of the bone plate barrel portion. In one specific example, an impact force on the distal end of the locking collar frictionally locks the tapered outer surface of the locking collar to the tapered inner surface of the bone plate internal bore, preventing further rotation of the collar relative to the bone plate, and thereby preventing further rotation of the lag screw relative to the bone plate. This frictional locking is known as the Morse Taper effect. The components described above (i.e., lag screw, bone plate, locking collar) may be formed of any bio-compatible material, but are preferably of stainless steel, titanium alloy, or titanium.

Alternatively, the outer surface of the locking collar may be formed with a reverse taper defined by a major diameter and a minor diameter, a proximal end of the collar having the major diameter, and a distal end of the collar having the minor diameter. The locking collar, in the second position, may then be frictionally engaged in a proximal section of the internal bore of the bone plate by a force in a distal direction (i.e., a force directed away from, rather than toward, the patient's body), such as that applied with a slide-hammer.

The barrel portion of the bone plate may be angled relative to the flat portion, and the device may be configured and adapted for repair of fractures of the femoral neck (i.e., hip bone). It should be pointed out, however, that the device is generally applicable to any type of bone fracture where rotational stabilization is important. In addition, the locking collar may be formed with a plurality of partial lengthwise slots extending from a distal end of the collar toward the proximal end of the collar. The lag screw may be formed with a cancellous screw thread, or it may be formed with a plurality of helically twisted blades.

In one variation of this embodiment, the device may further comprise a threaded bore in the distal end of the lag screw, and a compression screw insertable into the threaded bore of the lag screw. When threaded into the threaded bore of the lag screw, the compression screw abuts a distal end of the locking collar and draws the lag screw in an axial direction to join the two bone segments and reduce the fracture. As with the elements discussed above, the compression screw may be formed of stainless steel, titanium alloy, or titanium.

In another embodiment, the invention is a device for rotational stabilization of bone segments comprising: a bone lag screw having a bone-engagement end and a distal end, the bone-engagement end configured for engaging a first bone segment; a bone plate having a flat portion for engaging a second bone segment and a barrel portion having an internal bore for slidably receiving the lag screw, part of the internal bore having a taper; and a cylindrical locking collar having a hollowed cylindrical interior, a keyed internal profile that mates with the keyed cross-sectional profile of the lag screw to rotationally couple the locking collar and the lag screw when the lag screw is inserted through the locking collar, and a tapered outer surface configured and dimensioned for (1) free rotation, in a first position, within the internal bore of the bone plate barrel portion and (2) frictionally engaging, in a second position, the internal bore of the bone plate barrel portion to resist or prevent rotation of the collar relative to the bone plate, and thereby resist or prevent rotation of the lag screw relative to the bone plate. An impact force on the distal end of the locking collar frictionally locks the tapered outer surface of the locking collar to the tapered inner surface of the bone plate internal bore, preventing further rotation of the collar relative to the bone plate, and thereby preventing further rotation of the lag screw relative to the bone plate. This frictional locking is known as the Morse Taper effect. The taper of the outer surface of the locking collar may range from about 0 degrees to about 10 degrees, and may be defined by a major diameter and a minor diameter, a distal end of the collar having the major diameter, and a proximal end of the collar having the minor diameter. The barrel portion of the bone plate may be angled relative to the flat portion, and the device may be configured and adapted for repair of fractures of the femoral neck (i.e., hip bone), but is generally applicable to any type of bone fracture where rotational stabilization is important. The components described above (i.e., lag screw, bone plate, locking collar) may be formed of any biocompatible material, but are preferably formed of stainless steel, titanium alloy, or titanium. In addition, the locking collar may be formed with a plurality of partial lengthwise slots extending from the distal end of the collar toward the proximal end of the collar. The taper of the outer surface of the locking collar may be of the same degree and profile as the taper of the internal bore of the angled barrel portion.

In an alternative arrangement, the outer surface of the locking collar may be formed with a reverse taper defined by a major diameter and a minor diameter, a proximal end of the collar having the major diameter, and a distal end of the collar having the minor diameter. The locking collar, in the second position, may then be frictionally engaged in a proximal section of the internal bore of the bone plate by a force in a distal direction (i.e., a force directed away from, rather than toward, the patient's body), such as that applied with a slap-hammer.

The device may further comprise a threaded bore in the distal end of the lag screw, and a compression screw insertable into the threaded bore of the lag screw. When threaded into the threaded bore of the lag screw, the compression screw abuts the distal end of the locking collar and draws the lag screw in an axial direction to join the two bone segments and reduce the fracture. As with the elements discussed above, the compression screw may be formed of stainless steel, titanium alloy, or titanium.

In still another preferred embodiment, the invention provides an improved method for rotationally stabilizing bone segments utilizing a bone lag screw and a bone plate, the improvement comprising: sufficiently locking the bone screw to the bone plate by frictional engagement to rotationally stabilize the bone segments relative to one another. The method may further comprise: inserting a locking collar into a barrel portion of a bone plate; inserting a lag screw through the locking collar and barrel portion; rotationally coupling the locking collar and the lag screw; attaching the bone-engagement end of the lag screw to a first bone segment; and impacting the locking collar to frictionally engage an outer surface of the locking collar to the internal bore to resist or prevent further rotation of the collar relative to the bone plate, and thereby prevent further rotation of the lag screw relative to the bone plate.

BRIEF DESCRIPTION OF THE DRAWINGS

The present invention will be understood and appreciated more fully from the following detailed description, taken in conjunction with the drawings in which:

FIG. 1 is an isometric view of the disassembled components of the device in a preferred embodiment of the present invention.

FIG. 2 is a cross-sectional view of the bone plate and locking collar of the present invention.

FIG. 3A is a cross-sectional view of the locking collar of the present invention.

FIG. 3B is a plan view of the locking collar of the present invention.

DETAILED DESCRIPTION OF THE PREFERRED EMBODIMENTS

Reference is now made to FIG. 1, which is an isometric view of the disassembled components of the device of the present invention. The device allows a lag screw (or hip screw) to be aligned and rotationally locked within the bore of a bone repair plate. While the device is described in the context of hip fracture repair, it should be pointed out that the device may also be used in the repair of other bone fractures, such as knee joint fractures.

Figure 5:
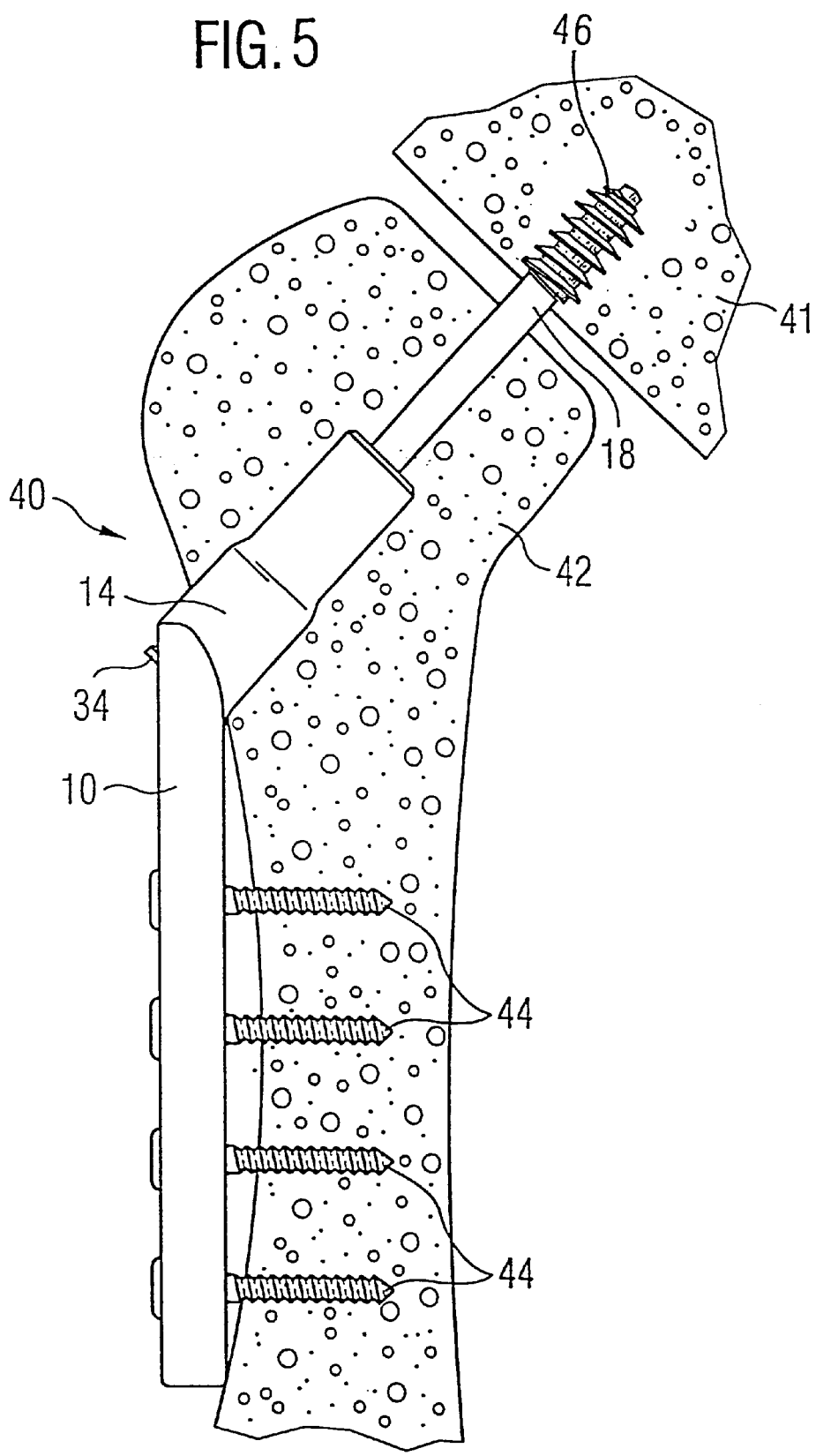
FIG. 5 is a cross sectional view through a pair of bone segments demonstrating the application of another embodiment of the device of the present invention.

A side plate 10 has a flat portion 12 for attachment to the femur shaft (not shown) and an angled barrel portion 14 having an internal bore 16. The flat portion 12 has holes 15 (which may be self-compressing screw holes) for connection to the femoral shaft using screws or other coupling means. The internal bore 16 is formed with a taper or cone, as will be explained below with reference to FIG. 2. A lag screw 18 has a drilling portion 20 at a bone-engagement end and a threaded internal bore 22 at a distal end. The lag screw 18 may be formed with a conventional cancellous screw thread 46 (as shown in FIG. 5), or may be formed with a plurality of helically twisted blades (as shown in FIG. 1), for example such as that disclosed in U.S. Pat. No. 5,741,256 to Bresina, incorporated herein by reference. With regard to the descriptions of the elements of the present invention, it should be pointed out that the terms "proximal" and "distal" are defined with relation to the body of the patient (i.e., the person receiving the bone stabilization device). For example, the term "proximal" is used to describe that portion of a given element closer to the center of the patient's body, and the term "distal" refers to that portion of the element further away from the center of the patient's body.

A locking collar 24 has a hollow cylindrical interior and an outer surface 26 formed with a taper. The taper of the outer surface 26 of locking collar 24, ranging from about 0 degrees to about 10 degrees, is of the same degree and profile as the taper of the internal bore 16. The locking collar 24 also has a circumferential lip 28 (see FIG. 3A) at a distal end that mates with a circumferential groove 30 at a distal end of the internal bore 16. When the locking collar 24 is introduced into the internal bore 16, the circumferential lip 28 engages the circumferential groove 30, such that the collar is axially restrained in the bore, but is free to rotate with respect to the bore. It should be noted that the bone stabilization device may be supplied to physicians with the locking collar already engaged in the circumferential groove 30 of the bone plate internal bore 16. The locking collar also has a keyed internal profile, as will be explained below with reference to FIG. 3B, that mates with a keyed cross-sectional profile 32 on the shaft of the lag screw 18, to rotationally couple the locking collar 24 to the lag screw 18 when the lag screw is inserted through the internal bore 16 and the locking collar 24. The locking collar 24 also facilitates the proper alignment of the lag screw 18 and side plate 10, while simultaneously permitting the screw 18 to rotate freely so that it can engage the bone segment during installation. This integral alignment function of the locking collar 24 eliminates the need for additional components or alignment tools.

After the locking collar 24 is placed within bore 16, and the lag screw 18 is inserted through the collar and has satisfactorily engaged the bone, an impact force is applied to the exposed end of the collar (i.e., the distal end), causing the lip 28 to become disengaged from the groove 30, and driving the collar proximally inward along the bore 16, resulting in the tapered outer surface 26 of the locking collar becoming frictionally locked with the tapered surface of the internal bore 16. This frictional locking, known as the Morse Taper effect, prevents further movement (both axial and rotational) of the collar 24 relative to the internal bore 16, and so prevents further rotation of the lag screw 18. This rotational stabilization of the lag screw relative to the bone plate will prevent premature wear of the bone fragments and loosening of the system prior to complete bone healing.

It should be noted that in an alternate embodiment, the bore may have a reverse taper, as compared to that of the embodiment illustrated in the figures herein. In this embodiment, the bore has its major diameter at the proximal end, its minor diameter at the distal end, and the collar 24 is locked in place at the proximal end of the internal bore 16 by a force in the distal direction, such as that applied by a slide-hammer.

At this point, the lag screw is rotationally fixed relative to the side plate 10 and locking collar 24, but the lag screw may still slide axially relative to the collar and side plate. A compression screw 34 may be inserted into the threaded bore 22 of the lag screw, abutting the distal end of the locking collar 24 and drawing the lag screw axially in the distal direction, to join the separated bone segments (i.e., reducing the fracture) and promote the desired healing. The elements described above may be formed of stainless steel, titanium alloy, titanium, or any other material with suitable strength and bio-compatibility.

Reference is now made to FIG. 2, which is a cross-sectional view of the side plate and locking collar of the present invention. As discussed above, the side plate 10 has a flat portion 12 for connection to the femoral shaft and an angled barrel portion 14 having an internal bore 16 for slidably receiving a lag screw (not shown). The bore 16 has a tapered surface 17 along part of its length. A locking collar 24 sits within the internal bore 16, a circumferential lip 28 on the collar 24 rotatably engaging a circumferential groove 30 on the bore 16. The collar 24 has a tapered outer surface 26, with the same degree and profile as the tapered surface 17 of internal bore 16. Prior to insertion and alignment of the lag screw (not shown) and application of an impact force to the distal end 19 of the collar, the collar can rotatably slide within the bore 16. The collar 24 has a keyed internal profile 21, as shown most clearly in FIG. 3B, for mating and rotationally coupling with a corresponding keyed cross-sectional profile of the lag screw. Thus, upon insertion of the lag screw through the bore 16 and collar 24, rotation of the lag screw causes rotation of the locking collar 24 relative to the bore 16. Upon application of an impact force to distal end 19 of the collar, the tapered outer surface 26 of the collar becomes frictionally locked with tapered surface 17 of bore 16. As described above, this is known as the Morse Taper effect.

Reference is now made to FIGS. 3A and 3B, which are sectional and plan views, respectively, of the locking collar of the present invention. Locking collar 24 has a tapered outer surface 26, with a distal end 19, having the major diameter, and a proximal end 23, having the minor diameter. The distal end comprises a flat outer face designed to correspond to the flat underside of the head of a compression screw (not shown). A circumferential lip 28 is provided at distal end 19 for engaging a groove on the internal bore of the side plate (see FIGS. 1 and 2). Collar 24 also has a keyed internal profile 21, for mating with a corresponding keyed cross-sectional profile on the lag screw (not shown), and a plurality of lengthwise slots 27 extending from the distal end 19 toward the proximal end 23. These slots 27 facilitate disengagement of the circumferential lip 28 from the circumferential groove on the internal bore of the side plate (not shown), after the lag screw is satisfactorily engaged with the bone. As discussed above, the collar 24 facilitates alignment and ensures proper orientation of the lag screw, while allowing the screw to rotate freely so that its drilling portion 20 can engage its respective bone fragment during installation. An impact force subsequently applied to distal end 19 frictionally locks the tapered outer surface 26 to the mating tapered surface of the side plate internal bore (see FIG. 2). The locking collar may be formed of stainless steel, titanium, or any other material with suitable strength and bio-compatible characteristics.

Figure 4:
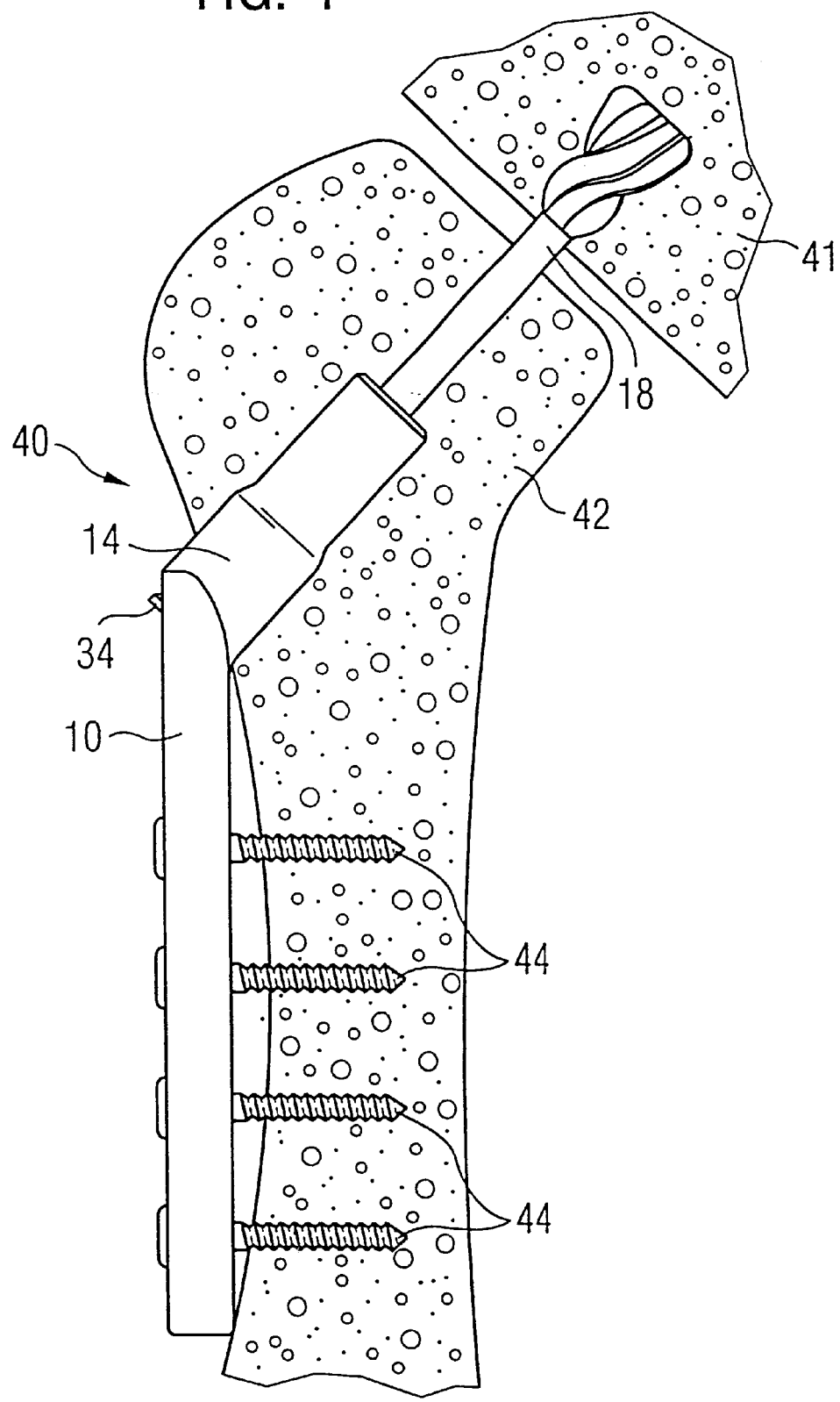
FIG. 4 is a cross-sectional view through a pair of bone segments demonstrating the application of the device of the present invention.

Reference is now made to FIG. 4 which demonstrates the application of the device of the present invention to repair a fracture of the femoral neck (i.e., hip). As shown, the assembled device 40 is used to join two bone segments 41, 42 (i.e., the femoral head and the femoral shaft). A lag screw 18 having a bone-engagement end, a distal end, and a keyed cross-sectional profile over part of its length is provided. The bone-engagement end of lag screw 18 is configured for engaging first bone segment 41 and the distal end has a threaded bore.

A side plate 10 is provided having a flat portion for engaging second bone segment 42 and an angled barrel portion 14 with an internal bore for slidably receiving the lag screw. A portion of the internal bore (not shown) has a taper and a distal end of the internal bore has a circumferential groove.

A cylindrical locking collar (not shown) is also provided. The collar has a hollowed cylindrical interior, an outer surface formed with a taper defined by a major diameter and a minor diameter, a distal end of the collar having the major diameter, a proximal end of the collar having the minor diameter, a circumferential lip at the distal end for engaging the circumferential groove of the internal bore, and a keyed internal profile.

The system is assembled by inserting the cylindrical locking collar into the internal bore of the bone plate so that it rotatably engages the internal bore. As discussed above, the system may be supplied to physicians with the locking collar already engaged in the internal bore of the bone plate, thus eliminating the need for physicians or technicians to insert the collar into the bore of the bone plate. The lag screw 18 is inserted into the locking collar, such that the keyed cross-sectional profile of the lag screw mates with the keyed internal profile of the locking collar to rotationally couple the locking collar and the lag screw. After proper engagement of the lag screw 34 with the first bone segment 41, the distal end of the locking collar (not shown) is impacted using a mallet-type instrument, frictionally locking the collar within the angled barrel portion 14 of the side plate 10. This frictional locking, known as the Morse Taper effect, prevents further rotation of the collar relative to the bone plate, and thereby prevents further rotation of the lag screw relative to the bone plate. In an alternative arrangement, the collar is locked in place by a force in the distal direction, such as that applied by a slap-hammer. The side plate 10 would typically be anchored to the femoral shaft 42 using bone screws 44 (formed of stainless steel or titanium alloy). A compression screw 34 would then be inserted into the threaded bore (see FIG. 1) of the lag screw, abutting the locking collar and axially drawing bone segment 41 toward bone segment 42

(see FIG. 4). Alternatively, the side plate 10 may be affixed to the femoral shaft prior to impact of the locking collar.

While the present invention has been described with reference to the preferred embodiments, those skilled in the art will recognize that numerous variations and modifications may be made without departing from the scope of the present invention. This is especially true with regard to the shape and configuration of the bone plate and lag screw, which can be adjusted according to the type and location of the bone segments to be joined. Accordingly, it should be clearly understood that the embodiments of the invention described above are not intended as limitations on the scope of the invention, which is defined only by the following claims.

What is claimed is:

1. A device for rotational stabilization of bone segments comprising:
   a bone lag screw having a bone-engagement end, a distal end, and a keyed cross-sectional profile, the bone-engagement end configured for engaging a first bone segment;
   a bone plate having a flat portion for engaging a second bone segment and a barrel portion having an internal bore for slidably receiving the lag screw; and
   a locking collar having a keyed internal profile that mates with the keyed cross-sectional profile of the lag screw to rotationally couple the locking collar and the lag screw when the lag screw is inserted through the locking collar, and an outer surface configured and dimensioned for (1) free rotation, in a first position within the internal bore of the bone plate barrel portion and (2) frictionally engaging, in a second position, the internal bore of the bone plate barrel portion to resist or prevent rotation of the collar relative to the bone plate, and thereby resist or prevent rotation of the lag screw relative to the bone plate.

2. The device of claim 1, wherein the locking collar is cylindrical.

3. The device of claim 2, wherein the outer surface of the locking collar is formed with a taper.

4. The device of claim 3 wherein the taper of the outer surface of the locking collar is less than about 10 degrees.

5. The device of claim 3, wherein the internal bore of the bone plate barrel portion is formed with a taper and the taper of the outer surface of the locking collar is of the same degree and profile as the taper of the internal bore of the bone plate barrel portion.

6. The device of claim 3, wherein the taper of the outer surface of the locking collar is defined by a major diameter and a minor diameter, a distal end of the collar having the major diameter, and a proximal end of the collar having the minor diameter.

7. The device of claim 2, wherein the outer surface of the locking collar is formed with a reverse taper defined by a major diameter and a minor diameter, a proximal end of the collar having the major diameter, and a distal end of the collar having the minor diameter.

8. The device of claim 7, wherein the locking collar, in the second position, is frictionally engaged in a proximal section of the internal bore of the bone plate by a force in a distal direction.

9. The device of claim 2, wherein the locking collar is formed with a plurality of partial lengthwise slots.

10. The device of claim 1, wherein the barrel portion of the bone plate is angled relative to the flat portion, the first bone segment is the femoral head, the second bone segment is the femoral shaft, and the device is configured and adapted for repair of fractures of the femoral neck.

11. The device of claim 1, wherein the lag screw is formed with a cancellous screw thread.

12. The device of claim 1, wherein the lag screw is formed with a plurality of helically twisted blades.

13. The device of claim 1, wherein the lag screw, bone plate, and locking collar are formed of stainless steel, titanium alloy, or titanium.

14. The device of claim 1, further comprising:
   a threaded bore in the distal end of the lag screw; and
   a compression screw insertable into the threaded bore of the lag screw.

15. The device of claim 14, wherein the compression screw, when threaded into the threaded bore of the lag screw, abuts a distal end of the locking collar and draws the lag screw in an axial direction to join the two bone segments.

16. The device of claim 14, wherein the compression screw is formed of stainless steel, titanium alloy, or titanium.

17. A device for rotational stabilization of bone segments comprising:
   a bone lag screw having a bone-engagement end, a distal end, and a keyed cross-sectional profile, the bone-engagement end configured for engaging a first bone segment;
   a bone plate having a flat portion for engaging a second bone segment and a barrel portion having an internal bore for slidably receiving the lag screw, part of the internal bore having a taper; and
   a cylindrical locking collar, having a hollowed cylindrical interior, a keyed internal profile that mates with the keyed cross-sectional profile of the lag screw to rotationally couple the locking collar and the lag screw when the lag screw is inserted through the locking collar, and a tapered outer surface configured and dimensioned for (1) free rotation, in a first position, within the internal bore of the bone plate barrel portion and (2) frictionally engaging, in a second position, the internal bore of the bone plate barrel portion to resist or prevent rotation of the collar relative to the bone plate, and thereby resist or prevent rotation of the lag screw relative to the bone plate.

18. The device of claim 17, wherein the barrel portion of the bone plate is angled relative to the flat portion, the first bone segment is the femoral head, the second bone segment is the femoral shaft, and the device is configured and adapted for repair of fractures of the femoral neck.

19. The device of claim 17, wherein the taper of the outer surface of the locking collar is less than about 10 degrees.

20. The device of claim 17, wherein the taper of the outer surface of the locking collar is of the same degree and profile as the taper of the internal bore of the angled barrel portion.

21. The device of claim 17, wherein the tapered outer surface of the locking collar is defined by a major diameter and a minor diameter, a distal end of the collar having the major diameter, and a proximal end of the collar having the minor diameter.

22. The device of claim 17, wherein the outer surface of the locking collar is formed with a reverse taper defined by a major diameter and a minor diameter, a proximal end of the collar having the major diameter, and a distal end of the collar having the minor diameter.

23. The device of claim 22, wherein the locking collar, in the second position, is frictionally engaged in a proximal section of the internal bore of the bone plate by a force in a distal direction.

24. The device of claim 17, wherein the locking collar is formed with a plurality of partial lengthwise slots extending from a distal end of the collar toward a proximal end of the collar.

25. The device of claim 17, wherein the lag screw, bone plate, and locking collar are formed of stainless steel, titanium alloy, or titanium.

26. The device of claim 17, further comprising:
a threaded bore in the distal end of the lag screw; and
a compression screw insertable into the threaded bore of the lag screw.

27. The device of claim 26, wherein the compression screw, when threaded into the threaded bore of the lag screw, abuts a distal end of the locking collar and draws the lag screw in an axial direction to join the two bone segments.

28. The device of claim 26, wherein the compression screw is formed of a stainless steel, titanium alloy, or titanium.

29. The device of claim 17, further comprising a circumferential groove at a distal end of the internal bore of the bone plate barrel portion, and a circumferential lip at a distal end of the locking collar for engaging the circumferential groove of the internal bore such that the collar freely rotates within the internal bore of the barrel in the first position.

30. In a method for rotationally stabilizing bone segments utilizing a bone lag screw and a bone plate, the improvement comprising:
sufficiently locking the bone screw to the bone plate by frictional engagement to rotationally stabilize the bone segments relative to one another.

31. The method of claim 30, further comprising:
inserting a locking collar into a barrel portion of a bone plate;
inserting a lag screw through the locking collar and barrel portion, rotationally coupling the locking collar and the lag screw;
attaching the bone-engagement end of the lag screw to a first bone segment; and
impacting the locking collar to frictionally engage an outer surface of the locking collar to internal bore to resist or prevent further rotation of the collar relative to the bone plate, and thereby prevent further rotation of the lag screw relative to the bone plate.

* * * * *